(12) United States Patent  
Gao

(10) Patent No.: US 8,543,234 B2  
(45) Date of Patent: Sep. 24, 2013

(54) METHOD AND SOFTWARE SYSTEM FOR TREATMENT PLANNING AND SURGICAL GUIDE CAD/CAM

(75) Inventor: Fei Gao, Cypress, CA (US)

(73) Assignee: Fei Gao, Cypress, CA (US)

( * ) Notice: Subject to any disclaimer, the term of this patent is extended or adjusted under 35 U.S.C. 154(b) by 444 days.

(21) Appl. No.: 12/795,045

(22) Filed: Jun. 7, 2010

(65) Prior Publication Data

US 2011/0301732 A1 Dec. 8, 2011

(51) Int. Cl.
*G06F 19/00* (2006.01)

(52) U.S. Cl.
USPC .......................................................... 700/97

(58) Field of Classification Search
USPC ............. 700/96, 97, 98; 703/1, 11; 433/215; 206/368
See application file for complete search history.

(56) References Cited

U.S. PATENT DOCUMENTS

2010/0105011 A1* 4/2010 Karkar et al. ................. 433/215

* cited by examiner

*Primary Examiner* — Kavita Padmanabhan
*Assistant Examiner* — Chad Rapp
(74) *Attorney, Agent, or Firm* — GuideMia Technologies

(57) ABSTRACT

A method and interactive computer system for dental implant treatment planning, surgical guide design and manufacturing. In the heart of the method is a fully associative workflow integrating image processing, treatment planning, surgical kit configuration and surgical guide CAD/CAM in one single computer system. In this workflow, any changes of image processing parameters and implant information in the earlier stage are automatically propagated to the downstream. This characteristic is referred as associativity. The software aspect of the system is built upon this concept and its corresponding data model. This invention also includes an image processing and geometric modeling approach that is characterized as design for manufacturability and applicability. The integration of treatment planning and surgical guide CAD is further on integrated with manufacturing equipment to constitute a complete CAD/CAM solution, which is also fully associative.

13 Claims, 16 Drawing Sheets

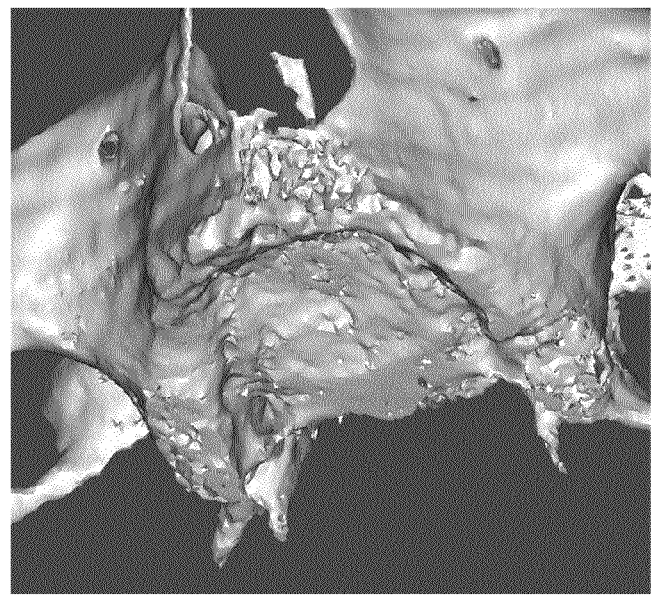
FIG. 9
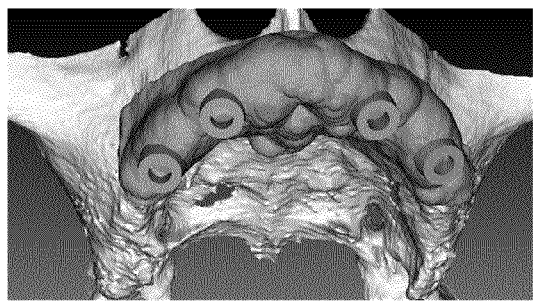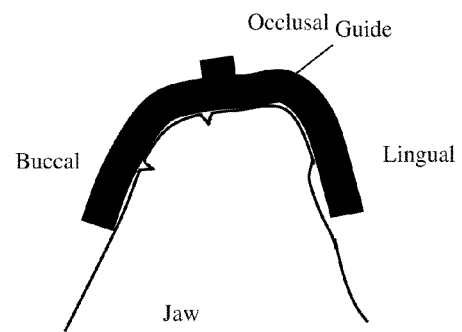
FIG. 10

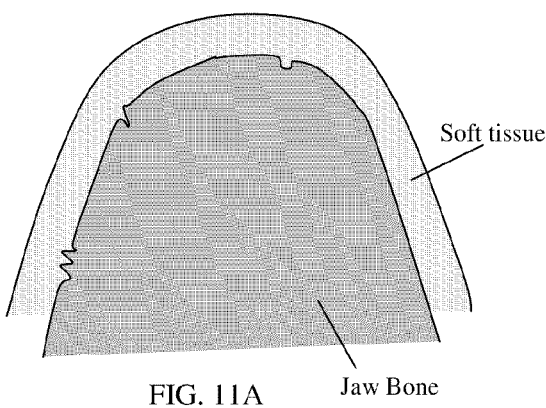
FIG. 11A   Jaw Bone / Soft tissue
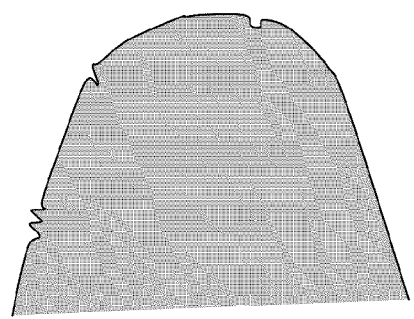
FIG. 11B
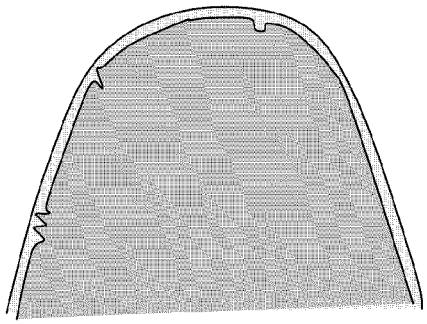
FIG. 11C
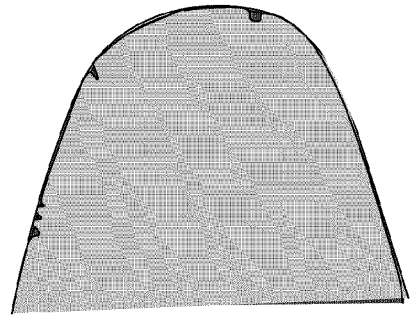
FIG. 11D
FIG. 11

```
class SITKTissuePeelingSimulation:public SITKProcessing
{
private:
        BinaryFilterType::Pointer binaryFilter;
        GrowFilterType::Pointer growfilter;
        PeelFilterType::Pointer peelfilter;
        SizeValueType radius;
        SMaskFilter *maskFilter;
        double in_outsideValue;
        double out_outsideValue;
public:
        SITKTissuePeelingSimulation(SignedImageType::Pointer input,
                SignedImageType::Pointer voi, double input_outside_value,
                double output_outside_value,double thickness)
        {
            binaryFilter = BinaryFilterType::New();
            binaryFilter->SetLowerThreshold(input_outside_value+1);
            binaryFilter->SetUpperThreshold(6000);
            binaryFilter->SetInput(input);
            binaryFilter->SetOutsideValue(0);
            binaryFilter->SetInsideValue(255);

growfilter = GrowFilterType::New();
            in_outsideValue = input_outside_value;
            out_outsideValue = output_outside_value;
            InputImageType::SizeType indexRadius;
            InputImageType::SpacingType spacing;
            spacing = input->GetSpacing();
            for (int i=0; i<3; i++)
            {
                    indexRadius[i] = thick/spacing[i];
            }
            StructuringElementType  structuringElement;
            structuringElement.SetRadius(indexRadius);
            structuringElement.CreateStructuringElement();
            growfilter->SetKernel( structuringElement );
            growfilter->SetInput(binaryFilter->GetOutput());

peelfilter = PeelFilterType::New();
            peelfilter->SetInput(growfilter->GetOutput());
            StructuringElementType  structuringElement1;
            structuringElement1.SetRadius(indexRadius);
            structuringElement1.CreateStructuringElement();
            peelfilter->SetKernel(structuringElement1 );

maskFilter = new SMaskFilter(voi, peelfilter->GetOutput(),
                    output_outside_value, false);
        };
        Void SetInput (SignedImageType::Pointer in)
         {
            binaryFilter->SetInput(in);
         };
        SignedImageType::PointerGetOutput ()
        {
            return maskFilter->GetOutput();
        };
};
```

FIG. 12

| | Implant OD | Mount OD | Sleeve Thickness | Sleeve Clearance | Sleeve Height | Elongation |
|---|---|---|---|---|---|---|
| P1 | 3.4 | 4 | 0.35 | 0.1 | 5 | 9 |
| P2 | 4.3 | 4.9 | 0.5 | 0.1 | 5 | 9 |
| P2 | 5 | 6.1 | 0.4 | 0.1 | 5 | 9 |
| P4 | 6 | 6.1 | 0.4 | 0.1 | 5 | 9 |
| P5 | | | | | | |
| P6 | | | | | | |
| P7 | | | | | | |
| P8 | | | | | | |
| P9 | | | | | | |
| P10 | | | | | | |
| P11 | | | | | | |
| P12 | | | | | | |
| P13 | | | | | | |
| P14 | | | | | | |

| | Implant OD | Sleeve Thickness | Sleeve Clearance | Sleeve Height | Elongation |
|---|---|---|---|---|---|
| P1 | 1.3 | 0.5 | 0.1 | 5 | 9 |
| P2 | 1.7 | 0.65 | 0.1 | 5 | 9 |
| P2 | 2 | 0.5 | 0.1 | 5 | 9 |
| P4 | 2.2 | 0.4 | 0.1 | 5 | 9 |
| P5 | 2.4 | 0.45 | 0.1 | 5 | 9 |
| P6 | 2.5 | 0.65 | 0.1 | 5 | 9 |
| P7 | 2.7 | 0.55 | 0.1 | 5 | 9 |
| P8 | 3 | 0.4 | 0.1 | 5 | 9 |
| P9 | 3.2 | 0.55 | 0.1 | 5 | 9 |
| P10 | 3.5 | 0.4 | 0.1 | 5 | 9 |
| P11 | 3.7 | 0.3 | 0.1 | 5 | 9 |
| P12 | 4 | 0.4 | 0.1 | 5 | 9 |
| P13 | 4.2 | 0.3 | 0.1 | 5 | 9 |
| P14 | 4.5 | 0.4 | 0.1 | 5 | 9 |

Implant A    Implant B

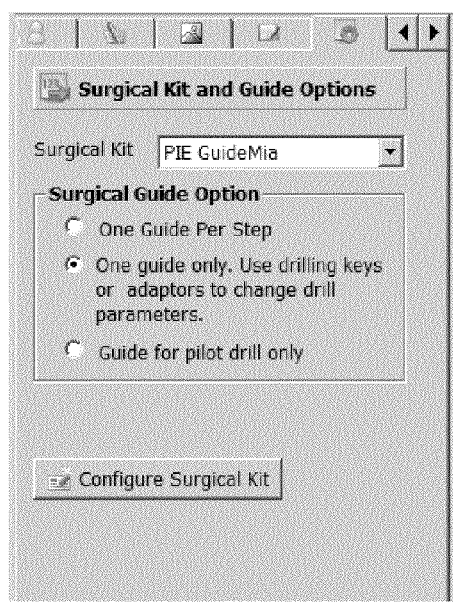
FIG. 20A
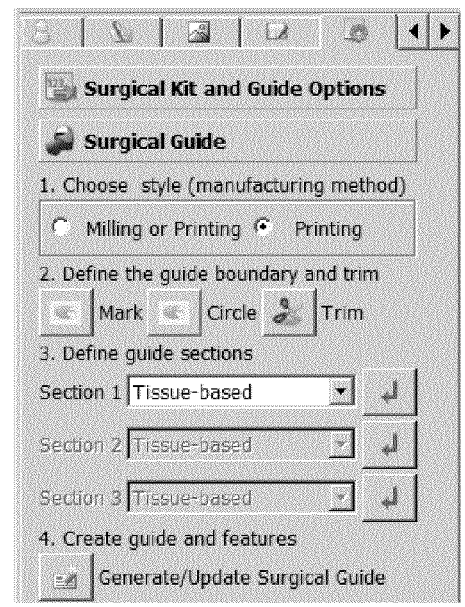
FIG. 20B
FIG. 20

METHOD AND SOFTWARE SYSTEM FOR TREATMENT PLANNING AND SURGICAL GUIDE CAD/CAM

CROSS-REFERENCE TO RELATED APPLICATIONS

U.S. patent application 12,776,544 May 10, 2010 Gao

REFERENCE CITED

U.S. Patent Docouments
  2007/0059665 A1 Mar. 15, 2007 Orentlicher
  2005/0148823 A1 Jul. 7 2005 Roose
  2009/0263764 A1 Oct. 22, 2009 Berckmans
  5,768,134 Jun. 16, 1998 Swaelens, et al.
  5,278,983 Jan. 11, 1994 Kawabe et al.
  5,689,711 Nov. 18, 1997 Bardasz
  6,105,041 Aug. 15, 2000 Bennett et al.
Other Publications
  Meagher, D. Geometric Modeling Using Octree Encoding. Computer Graphics and Image Processing, (Academic Press, Inc.), vol 19, pp.129-147, 1982.
  Tardieu PB, Vrielinck L, Escolano E, et al. Computer-assisted implant placement: scan template, simplant, surgiguide, and SAFE system. Int J Periodontics Rest Dent. 2007;27(2):141-149.
  Aztari A, Nikzad S.Computer-assisted implantology: historical background and potential outcomes-a review. Int J Med Robot. 2008 Jun;4(2):95-104.
  Jabero M, Sarment DP.Advanced surgical guidance technology: a review. Implant Dent. 2006 Jun;15(2):135-42.
  Spector L.Computer-aided dental implant planning. Dent Clin North Am. 2008 Oct;52(4):761-75, vi.

FIELD OF THE INVENTION

This invention concerns the method and software system for implant treatment planning and surgical guide CAD/CAM. This is for implant dentistry and also other fields that employ similar treatment planning and surgical guide concepts. This invention integrates image processing, treatment planning, surgical guide design, surgical kit configuration, design for manufacturing and CAM in a single fully associative workflow and system. In contrast, the surgical guide design and manufacturing in its current status is mainly happening in manufacturing facility as isolated step without integration with treatment planning.

BACKGROUND OF THE INVENTION

In implant dentistry, the procedure of image guided surgery is as following. An impression of a patient is taken at a dental office. It is then sent to a lab to make a radiographic guide (also known as scan template). The patient and the guide are sent to image center for CT or cone beam CT (CBCT) scan. The scan images are input into the treatment planning software that creates a treatment plan. Sometimes the radiographic guide is not necessary, so the treatment plan is just based on the patient's CT scan. The end result of treatment planning would be to design and make a surgical guide, a device with drilling sleeves for all the implants. It is placed onto patient's jawbone or mucosa at surgery time so that the surgeon can use it as a guide to drill holes for implant sites. If the treatment plan specifies, a surgical kit will be also used. Orentlicher et al. (US 2007/0059665 A1) described a similar procedure for obtaining patient image data for planning and/or placing dental implants. The patient is scanned at a radiology facility. Image data is then forwarded to a processing center and converted into a file of different format, which is later on forwarded to doctor's office for treatment planning.

In a typical dental implant planning system, a jawbone model, or a radiographic guide model if available, is used as a base for the surgical guide design. The user chooses the implant platforms (make, model and size), places implants as desired, and specifies a surgical kit to be used. The entire treatment plan with all of such information is sent to a manufacturing facility, where CAD operations are applied onto either the base model or even the filtered CT image data to create a surgical guide. The operations will create holes, inspection windows and other form features. The positions, orientations and sizes of implants, as well as the choice of the surgical kit, determine these modeling operations. The surgical guide is then made with CAM technology.

With almost all the dental implant planning systems, the treatment plans are sent to the vendors' facilities for further surgical guide design and manufacturing. The design and manufacturing happen behind the scene. The vendors mainly include NobelBiocare, Materialise, I-Dent, Keystone Dental, etc. Such a workflow is illustrated in FIG. 1. The review of the state-of-art treatment planning technologies can be found in the publications of Tardieu PB, Azari A, Jabero M, Spector L, etc. Some of them are listed in the references section.

One of the major disadvantages of this workflow is that the links between the steps are broken. When a doctor's office receives a processed model, they cannot do anything to change it. After they have started the planning, if they find the processed model doesn't well represent the patient's bone structure, they either keep going at a great risk without correcting the model, or request a new processing and hence lose their work. This problem also exists in the design of the surgical guide after the planning is done. Once the design starts, plan changes are not easy.

In this sequential workflow from image processing to treatment planning and then to surgical guide design, there is a pending issue that all the data and operation history should be kept, and any changes in an earlier stage can be propagated to later ones with the operations in later stages automatically updated. This is called an associative workflow or associativity in the workflow.

As far as surgical guide CAD/CAM is concerned, very rare information has been disclosed. Swaelens (U.S. Pat. No. 5,768,134) disclosed a method to make "perfected medical model" on the basis of medical image information with rapid prototyping technology. The approach starts with images of a part of the body of a patient by means of a CT scan or the like. Artificial functional elements corresponding to implant plans are added into the image data in a voxel-based method in the module that controls rapid prototyping. It was mentioned that the voxel based perfect model with functional elements could be converted to STL (triangle format) or moved into CAD systems to further add elements. This invention does not really concern a CAD approach commonly found in many industries, nor provides any user controls for the manipulation of the model. It provides some hybrid process of image processing, rapid prototyping, as well as modifying the image data with functional elements that are also voxel based. Since it encapsulates the operations to add form features by voxels into the rapid prototyping procedure, it does not integrate CAD and CAM in a conventional way where CAD and CAM are independent systems or modules. Also it is not clear how the "voxel-based" approach is used to add functional elements to the image data. In the final surgical guide model the smoothness/accuracy of the implant holes are much higher than CT data. In order to create holes like this, the voxels will have to be in the 20-40 microns range. However, the image data of the CT scan normally has voxel size of 200 microns up to 1 mm. It would be extremely computation extensive to reformat the CT scan to the acceptable accuracy.

In contrast, Keystone Dental directly drill holes and make other features off the radiographic guide. It is unknown if they actually performs CAD, CAM and the integration of the two.

Roose (US 2005/0148823) describes a method and system to design surgical guides for joint replacement prosthesis. The system includes a bone surface image generator, surgical guide image generator, and surgical guide image converter.

One of the major problems with surgical guide models of the state-of-the-art is the manufacturability and applicability. There are basically two categories of surgical guides. One is based on prefabricated radiographic guides. Another one is based on the bone structures segmented from patients' CT scans. Theoretically there can be a combination of the two approaches. Surgical guides are called tissue-borne for the first category, bone- or tooth-borne for the second. The manufacturability problem is mainly pertinent to the second. Swaelens did mention the perfected model could come from a scan template, but the invention in the way it is presented is mainly concerned of the bone- or tooth-borne guides. So does Roose's application.

It is problematic to design surgical guides based on bone structures hoping the guides will perfectly match the surfaces of the bone structures. Bone segmentation typically does not lead to a smooth model, especially when the patients don't have jaw bones that are dense enough. FIG. 9 shows that the actual bone structure has small dents or holes. This is not the worst case at all. There are situations that the bone quality is much more problem-prone. The surgical guide will have spikes or protrusions if made to match the surface of such a bone structure. It is necessary to cleanup the model in order to properly place it onto patients bone structure during surgery. This is one of the reasons that design of surgical guides will need to have the considerations for both manufacturability and applicability.

The accuracy of the surgical guide models is another critical issue. Due to many reasons, the reconstructed surface model of a scan template, or the contour surface of a bone structure, is barely accurate enough for the final surgical guide. Please see the application recently filed (Gao, 12,776,544). An iteration approach with calibration features is disclosed in that application, which also presents a legitimate reason that the associativity between image processing and guide design is necessary.

Another issue related to implant planning is the use of surgical kits. The introduction of surgical guides cannot be isolated from surgical kits. Implant surgical kits help the surgeons to drill holes with better orientation and depth control. Not like the old time that implants sites are all prepared with freehand drilling, nowadays surgical kits have components and features to ensure better operations. For example, adaptors or keys let the surgeon to fit different drills into one prepared hole, and thus facilitate sequential drilling without repositioning the tools. Drill stops, special features added to the drills, help the surgeons to control the depth of their drilling. As a result of using surgical kits, surgical guides are designed corresponding to the kits, and drill instructions are generated by treatment planning systems accordingly. More information about dental implant surgical kits can be found at NobelBiocare and other vendors' websites.

Software vendors typically let the users choose a platform of surgical kits, and generate the surgical guide models accordingly. The guide design is determined by both the treatment plan and the surgical kits chosen by the treatment planner. The popular approach is to design one surgical guide for each case. All the drilling sequences are performed with this guide and the selected surgical kits. Some systems only generate a guide for pilot drills, and let the surgeons do freehand drilling for the rest of the drilling sequences. Some systems generate multiple guides for a case, one guide for one drilling step of the sequences. More related information can be found in the websites of Materialise and NobelBiocare.

Berckmans, III et al. (US 2009/0263764 A1) introduces a method to design a surgical guide so that the surgical kit can certainly fit into the patient's mouth. The approach needs the patient's CT scan with mouth opened.

With the state-of-art techniques, users are not given the access to the computer aided design system of surgical guides, so what can be done is to just let users choose surgical kit platforms. In an open architecture and an integrated solution where the users are given the control to the entire planning and design process, there will be a need for the users to define or configure a surgical kit of their own, and adjust their guide design accordingly. For this purpose a universal definition of surgical kits is desired.

With prior art, one surgical kit is selected for one case, and the surgical guide is made for this kit. Sometimes, the guide is designed without the consideration of a kit simply because no kit is available. However, there can be situations that a doctor believes two implants of different models or even from different vendors need to be used in a single case. First, it can be for clinical reasons. The doctor decides to do so for the feasibility and survivability of the implants. The second reason can be that the patient's anatomical structure cannot accommodate certain surgical kit very well, or the guide model generated from the kit is considered not usable. Thirdly, surgical kits are normally designed for specific implant platforms, such as NobelBiocare's NobelReplace NP, RP, etc, thus are only applicable for the implants of given types and sizes. There are far more implant platforms than surgical kits, therefore there are scenarios that only some of the implants of a case can use surgical kits, or, scenarios that some implants may use one kit, some use another. Such scenarios have not been considered in prior art or publications yet. They don't happen very often, but are possible.

In summary, the following issues need to be resolved in order to have a good treatment planning solution. An associative workflow is desired to integrate image processing, treatment planning and surgical guide CAD/CAM. Surgical guide models need to be free from artifacts stemming from the patients bone density deficiency and structural problems so that the manufacturing of surgical guides can be done with common CAM solutions from RP to milling. An open architecture is needed for the users to configure their surgical kits in a universal way and for system to drive the guide design. This invention addresses these issues and develops approaches and software system to solve them.

BRIEF SUMMARY OF THE INVENTION

As above mentioned, a typical workflow of dental implant treatment planning is not fully integrated. Any changes to the earlier stage will cause the loss of work. The associative approach is invented to address this issue. Illustrated in FIG. 2, the workflow includes image processing, treatment planning, surgical kit configuration and selection, surgical guide design, etc. These components are not necessarily arranged in a sequential workflow, but they are all in an update pipeline and have access to a central data model.

Different from prior art is the associativity, which means the changes in this pipeline can be propagated to the downstream operations. This enables the users to review and modify their processing and plans in an integrated system without losing their planning and design intents. Even though the entire workflow can be performed at different facilities, the associative data model makes it possible to propagate changes from one to another. Surgical guide design no longer happens behind the scene. The users can fully control the design while maintaining the basic implant parameters.

The center of this invention is a fully associative data model, which records the workflows as steps or operations. Each operation is represented as parameters and outputs. It refers to the previous operations for inputs, and the outputs are used for succeeding operations. The project file, as the stored version of the data model, encapsulates the inputs, operations, and the outputs of the last operation.

The system status in this associative workflow and data model can be recorded as a snapshot—another component of this invention—together with visualization parameters, which not only records images of certain status for the purpose of further references, but also enables the system to re-enter this status and continue to work from there. This re-enterable snapshot differentiates itself from commonly found snapshot or bookmark approach.

The manufacturability and applicability issue—when bone or tooth structures are used as the base for surgical guide CAD—is another objective of this invention. It is not necessary to have the surgical guide model completely match the shape of the bone structure. Instead, the guide will only need to match some points to have an envelope that will enclose the bone structure as shown in FIG. 10. Other than using threshold filter to exclude every single voxel of soft tissue, this invention includes tissue peeling simulation to obtain a more practical bone model, which better serves as the base for surgical guide design.

Interestingly, this is aligned with the reality. During operations when patients' soft tissues need to be peeled and bone to be revealed, it does not make any sense to pick the gum till every bit. Instead, the tissues may remain in areas especially where bone has small concave areas.

The manufacturing of surgical guide models resulted from the bone models like this can use any technology from manual milling to rapid prototyping. Unlike Swaelen's method, surgical guide models designed by this method and made with rapid prototyping need virtually no post processing to deal with problematic areas corresponding to the small artifacts on bone structures, because they have been eliminated at the first place. The CAD/CAM integration offered by this invention is also fully associative.

A universal surgical kit definition is also included in this invention. The users or surgical kit venders can configure surgical kits of their own, and distribute their configuration files to others. A kit definition consists of a series of platforms, which basically correspond to the implant diameters. The definition is not for the manufacturing of surgical kits in this regard, but the design of surgical guides. Therefore the definition serves as a bridge between the design of guides and surgical kits. Each platform is defined by some parameters that will be affecting the guide design. The surgical kits made compliant with these parameters will be guaranteed to work with the surgical guides designed with the kits.

The algorithm to transfer the surgical kit definition into the parameters of form features is also part of this invention. In synergy with the concept of associativity, this approach enables the system to update surgical guide models automatically when the implant platforms and surgical kits are changed even after surgical guides have been designed.

Also in this invention is the hybrid mode of using surgical kits, which is developed for the situations that one or more surgical kits are used for one single case, or the situations that some implants will be using surgical kits, some won't. When no kit is used for an implant location, the surgical guide will be designed for only pilot drill at this location, but it will be still designed to use surgical kits for other locations.

DESCRIPTION OF THE DRAWINGS

FIG. 1-8 illustrates the concept, approach, data models and implementation of associative treatment planning and surgical guide design.

FIG. 1. The steps of an implant case using a scan template, or, radiographic guide, consisting of a workflow with isolated steps connected by file transferring.

FIG. 2. The integrated workflow with processing parameters connecting the pipeline. The entire pipeline can update together.

FIG. 3. The data model for associative design. The workflow consists of a series of time stamped nodes.

FIG. 4. An illustration of an object dependency graph. The dependency is encapsulated in the object hierarchy.

FIG. 5. The update of dependency graph.

FIG. 6. The history navigator.

FIG. 7. The data organization of the re-enterable snapshot.

FIG. 8. The snapshot navigator with thumbnails. A "make current" operation will let the system re-enter the system status when a snapshot is captured.

FIG. 9-13 shows another part of the invention—"design for manufacturability and applicability".

FIG. 9. The actual bone structure has small dents or holes if all the soft tissues are removed.

FIG. 10. The surgical guide should not be made match the surface of the bone in order to avoid spikes or undercuts. Illustrated with one cross section.

FIG. 11. The process to simulate the tissue peeling. FIG. 11A shows the image data.

FIG. 11B shows the filtered bone. FIG. 11C shows the model in FIG. 11B is grown. In FIG. 11D the model surface is then peeled.

FIG. 12. The class definition and code to set up the image processing pipeline of soft tissue peeling, with details omitted.

FIG. 13. The algorithm to generate the base model of a surgical guide from image processing, to perform feature-based modeling as well as the integration of design module and rapid prototyping.

FIG. 14-20 shows the surgical guide design driven by surgical kits.

FIG. 14. One implant location as an example to show the design of surgical guides. A surface model from radiographic guide is used as a base. Form features are added to the base model. Feature parameters depend on the implant size and the surgical kit to be used.

FIG. 15. An implementation of the surgical kit configuration. One kit includes a few platforms according to the implant platforms. Each platform is defined as implant mount diameter, outer diameter of the drilling sleeve, the mating gap between the sleeve and the drill, the drill elongation, etc.

FIG. 16. Another implementation of the surgical kit configuration.

FIG. 17. The hybrid use of surgical kits in one single case. Implant A with diameter 4.3 mm has a surgical kit corresponding to it, B doesn't. The surgical guide can be used for all the drilling sequence of A with the usage of the kit, but only pilot drill for B.

FIG. 18. This diagram illustrates the workflow that the surgical kit configuration tool is used to perform the conceptual design of a surgical kit.

FIG. 19. This shows the implant definition window, which is used to define implant library for treatment planning and for the workflow in FIG. 18.

FIG. 20. The screen captures of the tool to select surgical kit in FIG. 20A, and to design surgical guide in FIG. 20B.

DETAILED DESCRIPTION OF THE INVENTION

Figure 1:
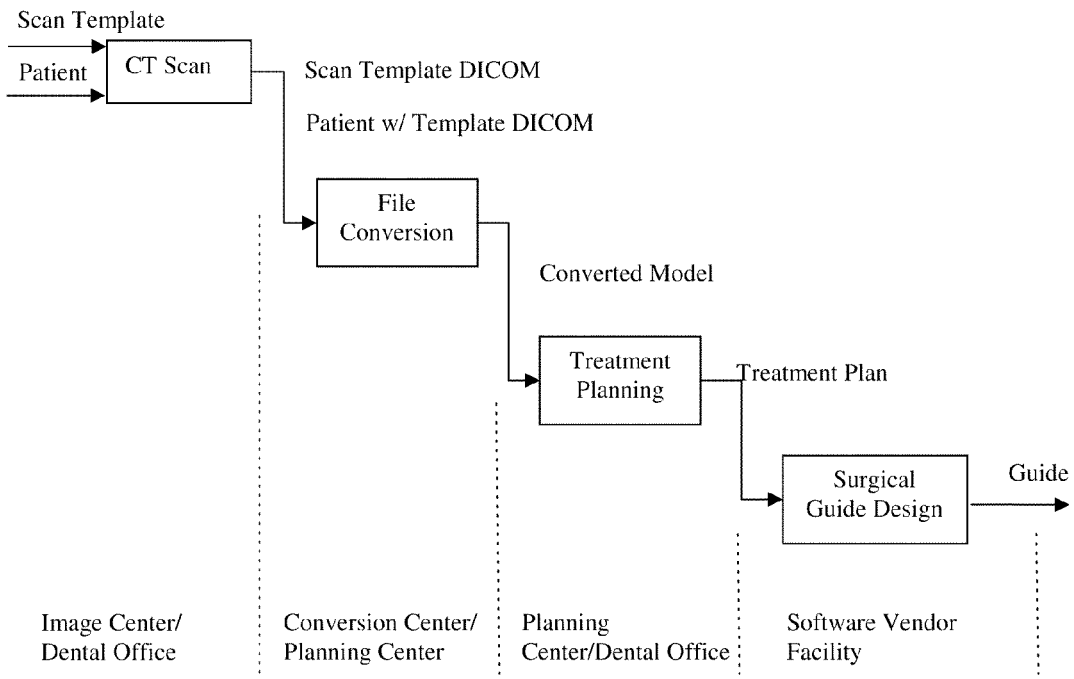
Figure 2:
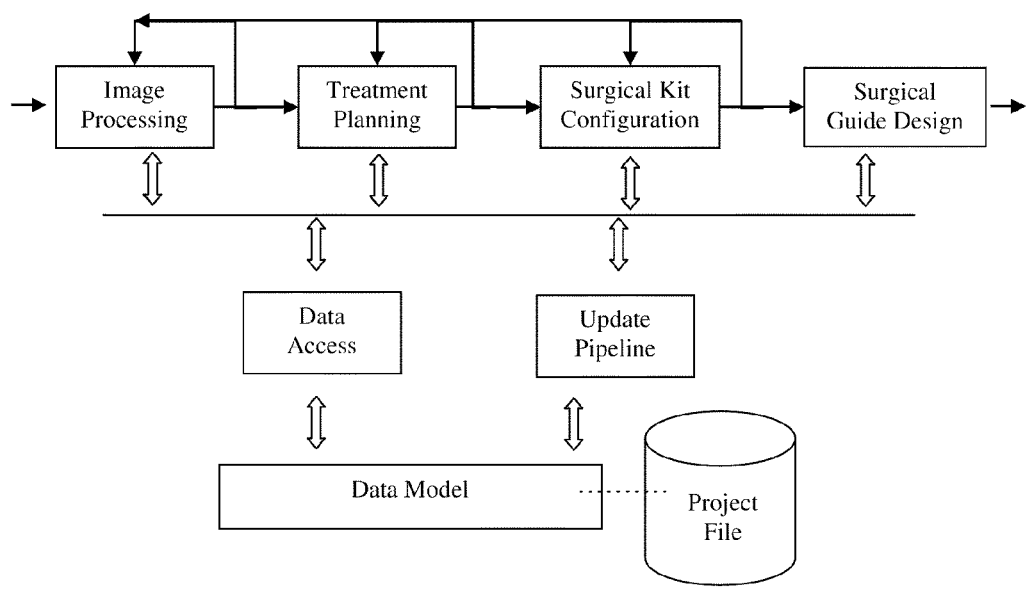

Associative Planning and Guide Design
Workflow

The workflow of the software system in this invention is characterized as the integration of image processing, surface reconstruction, computer-aided design, and surgical kit configuration as well. When using a scan template, or, radiographic guide, the workflow is as following:

1. A radiographic guide is made according to application US 2010/12,776,544. The patient is scanned wearing the radiographic guide, and then the guide is scanned alone.
2. The CT images of the patient wearing radiographic guide are input into the system. Image processing approaches are used to separate two models: the bone structure, and the markers on the radiographic guides.
3. The CT images of the radiographic guide are also imported into the system. The approach to segment the radiographic guide markers in step 2 is also used to get the markers in this scan.
4. The markers in step 3 are registered (or spatially aligned) with those in step 2.
5. A segmentation approach specifically designed for the radiographic guide design in US 2010/12,776,544 is used to segment and reconstruct a surface model of the radiographic guide.
6. The radiographic guide model is passed into the CAD module for surgical guide design.
7. A surgical kit driven approach is used to design surgical guide. Please refer to the next section for this technique.

A variation of this workflow as described following is for the so-called single scan protocol without radiographic guide, which generates bone- or tooth-level surgical guides.

1. The CT images of the patient are input into the system. Image processing approaches are used to segment the bone structure. The approach is described in the section "Design for Manufacturability and Applicability".
2. The bone structure is segmented as a result of simulating the soft tissue peeling, with which the reconstructed surface model will have fewer artifacts than that from a simple thresholding, and can thus better fit into the patient's mouth at the time of surgery.
3. A surface model of the bone structure is reconstructed and passed into the design module as the base of surgical guide design.
4. The geometric modeling of surgical guide driven by the surgical kit configuration is performed. Please refer to the next section for this technique.

Both of the above workflows integrate the steps of treatment planning and surgical guide design. There must be at least one step of the image processing, one step of surgical guide modeling, as well as the surgical kit driven design in this system.

The geometric modeling must be performed with operations based on boundary representation of surface models, such as trimming, Boolean, etc. There are two kinds of geometric modeling technology. One is based on boundary representation, such as U.S. Pat. No. 5,278,983 (Kawabe, et al.). One is voxel based, also known as space enumeration, or octree encoding. ("Geometric Modeling Using Octree Encoding" by D. Meagher, Computer Graphics and Image Processing, (Academic Press, Inc.), vol 19, pp. 129-147, 1982). Swaelens (U.S. Pat. No. 5,768,134) creates the functional features with voxel based approach.

Assiciativity

From the viewpoint of data handling, all the operations from image processing to surgical guide design constitute a data pipeline. This pipeline is saved and can be updated when changes happen. This automatic change propagation is made possible by the saved dependency data, or associativity, which refers to the concept that each and every single operations or steps are associative with the propagation mechanism.

This concept stemmed from computer aided design (CAD). U.S. Pat. No. 5,689,711 (Bardasz) is an example of the so-called associative design, where modeling operations are represented in an associative graph, or dependency graph. Nodes of a dependency graph are geometric features, edges the dependency between two features. In the CAD context, the associative operations basically apply to same data type, namely, geometric models being designed.

It needs to be pointed out that the associativity in our invention involves the integration of image processing, CAD and surgical kit configuration. It concerns the associativity of the entire workflow. The data objects being manipulated by the associative operations include 3D image, surface model, and form feature based modeling of the surgical guides.

A data model is designed for this purpose. It essentially has:

the operation history, which means all the steps and their parameters to process either the images or the surface models, the result of each step, which can be any data created by a step for other steps, for storage, or for display, and the dependency graph, which will be elaborated later.

Figure 3A:
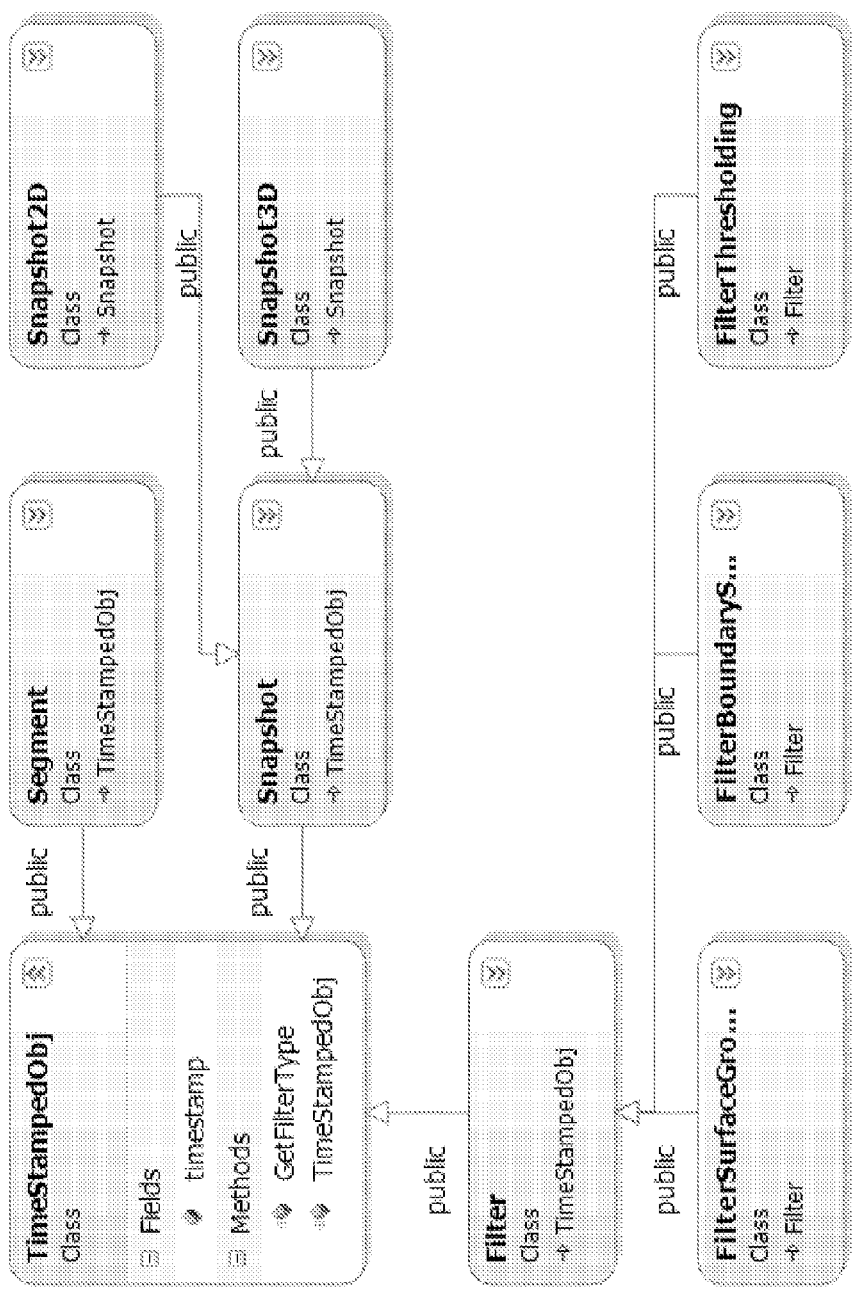
FIG. 3A shows the major objects are subclasses of TimeStampedObj, which essentially provides the update sequence of the data model.
Figure 3B:
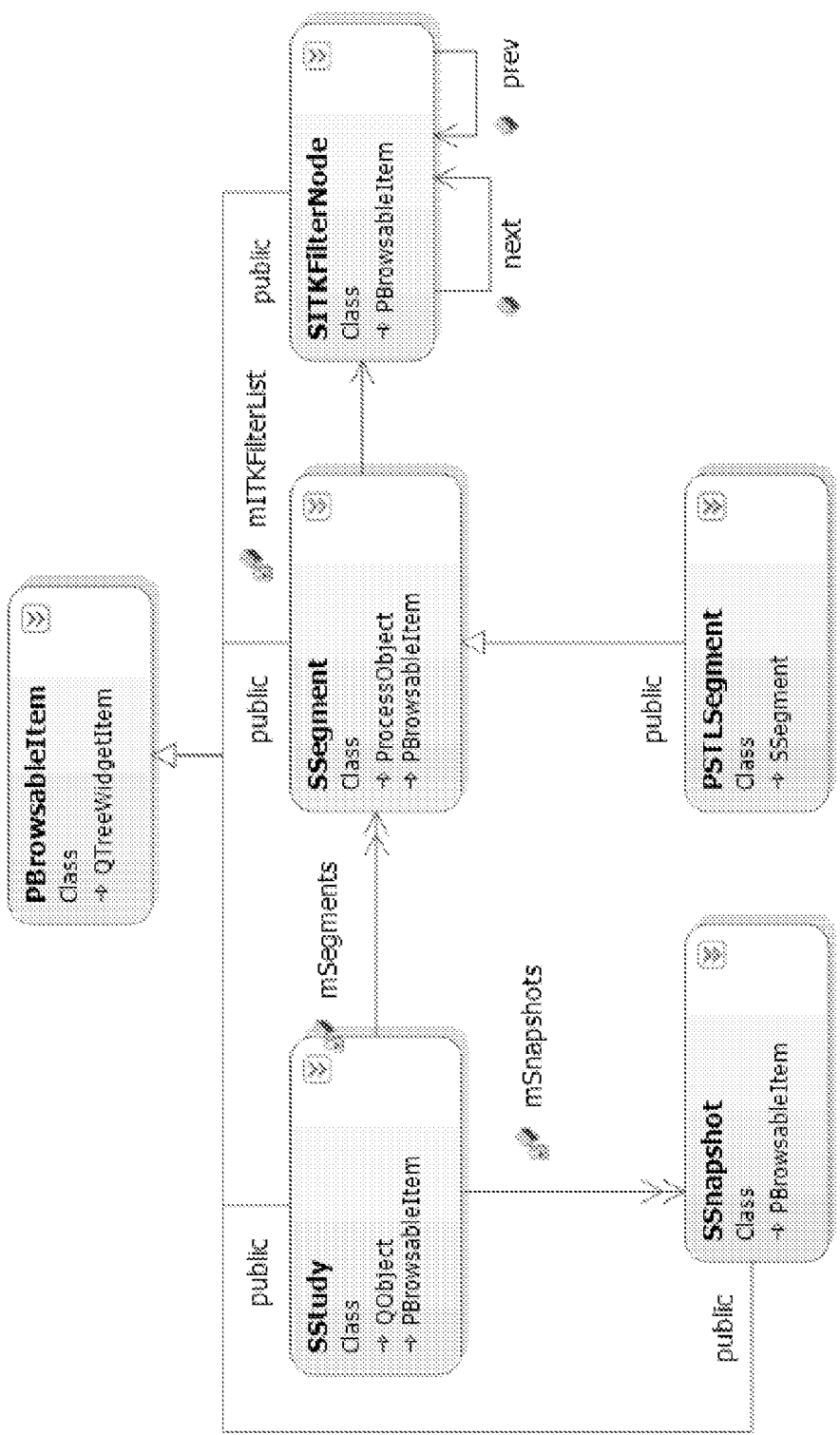
FIG. 3B is another aspect of the data model showing the top level objects that can be browsed in the object navigator of the software system.

FIGS. 3A and 3B show the data model of the workflow, or operation history using class SStudy. It consists of a series of SSegment and SSnapshot. SSegment is for any data object derived from input CT scan, normally, from a series of image segmentation steps. SSnapshot captures a snapshot of the workflow. More details will follow later.

They are all subclasses of SBrowsableItem, which is defined with parameters, references to previous nodes, timestamp, etc. It also has a status flag to indicate whether an object is temporarily suppressed (disabled) or enabled. The class SBrowsableItem provides the mechanism for a history navigator that is described later.

SSegment and SSnapshot also are subclasses of TimestampedObj. SSegment has a list of Filter, which are also time stamped. Filter and child classes have references pointing to previous and next nodes, so do SSegment and SSnapshot.

A specific child class of SSegment may also have its own local pipeline consisting of instances of the class Filter, which represents the sequence of lower level operations. For example, the operation to segment bone structure could include operations to extract a region of interest, to smooth the image data, to do a connected thresholding with given seed points, etc. These operations are encapsulated under one node, the bone segment. In the geometric modeling stage, one implant hole will include a set of operations to create features—a boss with flat top, a hole, and additional features that are needed to insert the drilling sleeve.

This associative workflow is especially suitable for the iterative image segmentation and surface reconstruction of the radiographic guides with calibration features described in the application US 2010/12,776,544 filed in the meantime. Moreover, this iterative process can happen even after the surgical guide design has been finished.

The project files corresponding to this data model are important for the workflow and associativity. Practically, those steps of afore-mentioned workflow can happen at different facilities with different users. The decisions of treatment planning and guide design are carried over from one site to another by the project files, which is an exported version of the internal data model.

Since all the decisions and intents are kept in project files, it is possible for the software users at any stage of the workflow to go back to earlier steps and make changes. This making the plan changes much easier even if the entire workflow is deployed as multiple sites.

With such a data model, the objects in a workflow are organized by timestamps, which indicate the temporal dependency of the objects, and thus provide a simple mechanism to update the workflow. When an object is changed, we can simply update the objects created after this object. A better update mechanism at finer granularity is however in the TimestampedObj class.

Dependency Graph

Figure 4A:
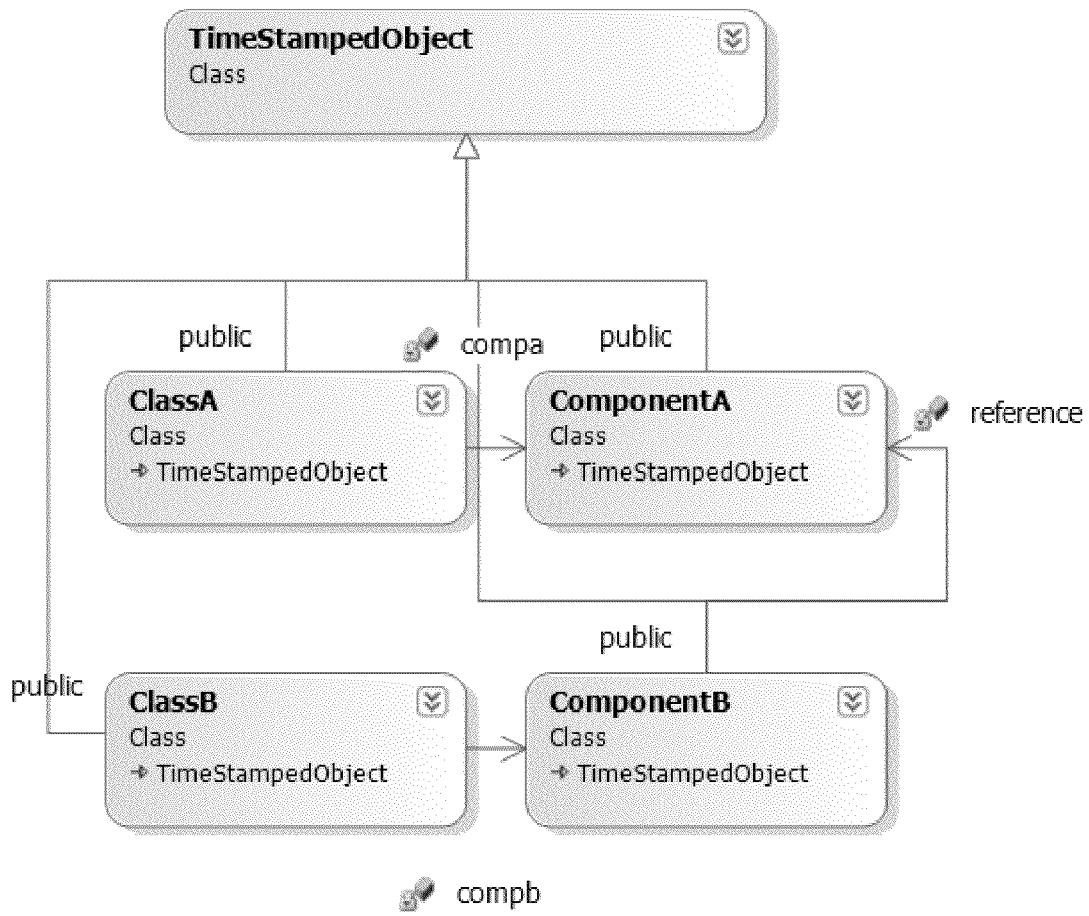
FIG. 4A shows the hierarchy in the object definition.

TimestampedObj can represent a dependency graph of a set of objects. FIG. 4A shows the concept of such graph. Object B has a component or attribute b, which refers to component or attribute a of object A. When component a is edited or deleted, B will be updated. In the computer-aided design area, this is translated to something like hole B is on the top of boss A. Component b and a are called face references or edge references. Within our workflow encapsulating image processing and CAD, the objects can be a definition of a region of interest, seed points, an image filter, an implant, etc, and this kind of dependencies have much more variants.

Figure 4B:
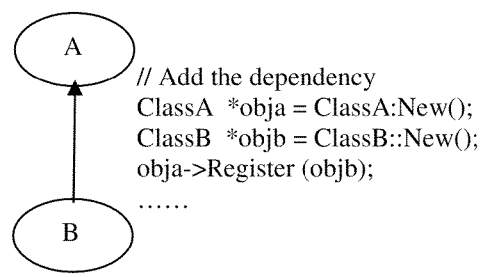
FIG. 4B is another example of the dependency graph. The dependency link is registered by a function call and stored explicitly in a data structure.

FIG. 4B also indicates an embodiment of the dependency graph. The dependency links between objects are represented by the pointers in the object hierarchy. The object hierarchy is traversed whenever it is needed to find out the dependencies among objects. This is called an implicit approach.

In order to implement the dependency graph in an explicit way, the idea of "smart pointer" is adopted. As in U.S. Pat. No. 6,105,041, "Smart pointer" is widely used in memory management and garbage collection with many different implementations. The basic idea is to register the reference between two objects when one is referring to another. A smart pointer has the conventions C/C++ object pointer and the mechanism to manage the reference count. When an object is deleted, the objects referred by this object via smart pointers will automatically reduce their reference counts. When the reference count of an object is 0, this object will be deleted.

FIG. 4B shows an embodiment of dependency graph using smart pointer. A register function is called when the reference between two objects are established. This register function explicitly adds a dependency link in the data model. All the links together make a dependency graph. With this explicit approach it is no longer necessary to maintain and track all the dependencies within the object definitions, hence the approach helps simplify the object hierarchy.

Behind the scene is a module to manage the dependency links and to update the graph whenever possible. Since all the relationships are explicitly represented as links between two objects, it is very easy to implement a reasoning engine to decide what need to be updated, either with forward reasoning or backward.

Figure 5:
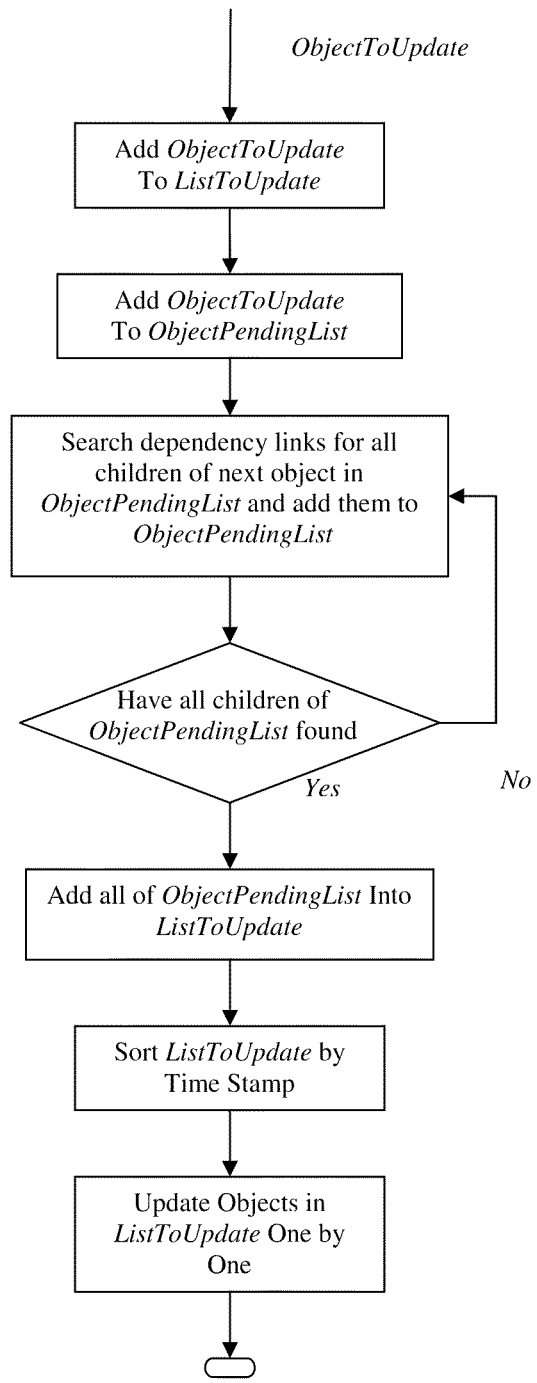

FIG. 5 is the workflow of the forward update of dependency graph. When an object is to be updated, it is added to a list ListToUpdate. The dependency links are traversed then, and all its children will also be added to this list. When there are no more children to add, the objects in ListToUpdate will be sorted by timestamp and then update in sequence.

History Navigator

Figure 6:
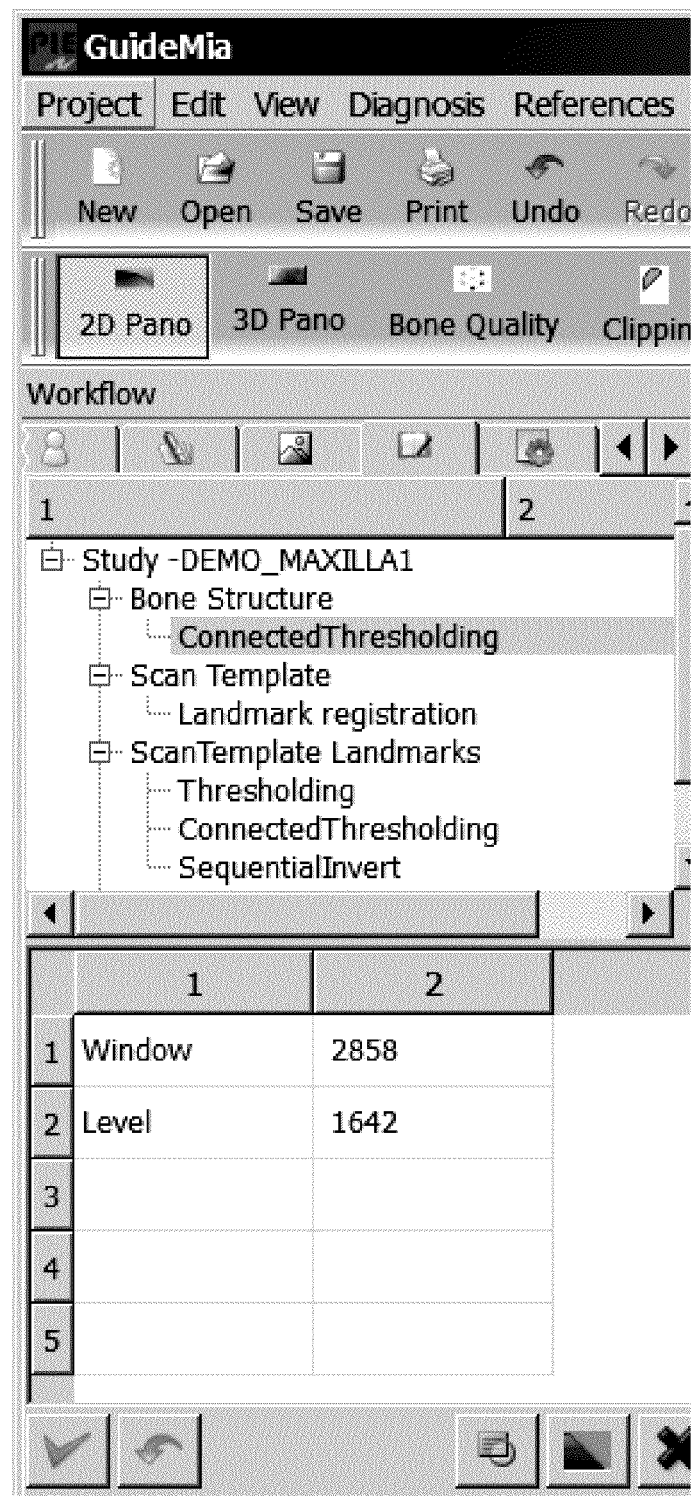

With the associative data model, the software system also features a history navigator and related functions to manipulate the history as shown in FIG. 6. The nodes of the navigator are the time stamped operations. This navigator distinguished itself from commonly found ones in many software systems in the following aspects:

It is a history navigator instead of an object navigator. There is a dependency graph and update pipeline behind it.

The history navigator includes the operations from both image processing and geometric modeling (CAD) in one system.

It serves the purpose of associative treatment planning and surgical guide design.

Context menu is defined for the nodes. It include deleting, suppress/unsuppress, editing, and other methods.

When an operation is deleted from the workflow, all of its children operations will need be deleted or re-attached to other nodes. The pipeline updates include two layers of work. In the higher level, the dependencies will be rebuilt with nodes reconnected. In the lower level all the affected nodes will be automatically updated. Deleting an implant is a typical example of this.

When the user wants to see how a surgical guide will look like without one of the implants, what he/she can do is another very useful operation—suppressing a node. When this implant is suppressed, the data remains, but corresponding features will be automatically removed from the surgical guide.

If necessary, the suppressed implant can be unsuppressed, meaning, brought back to life, which will of course trigger the update of the processing pipeline.

Of course, editing is one of the most important methods. Whenever an implant parameters or locations are edited, the surgical guide features will update accordingly.

Re-Enterable Workflow Snapshot

It is very common in a medical image processing system to save snapshots of image display windows in order to help the discussion and archiving of the medical cases. However, such static image capturing does not contain enough context information, and it is often time very hard for another party to figure out how the results are achieved.

Figure 7:
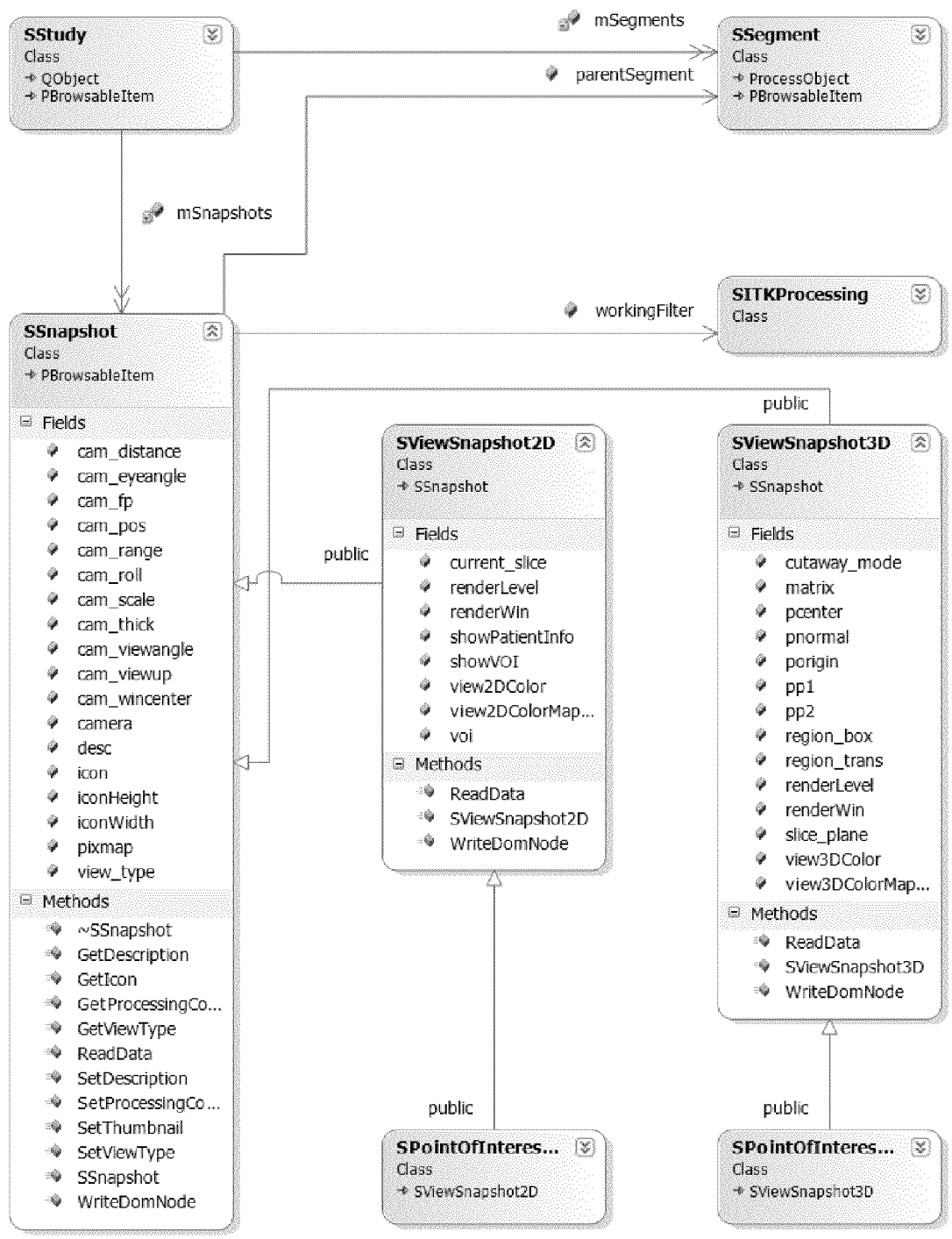
Figure 8:
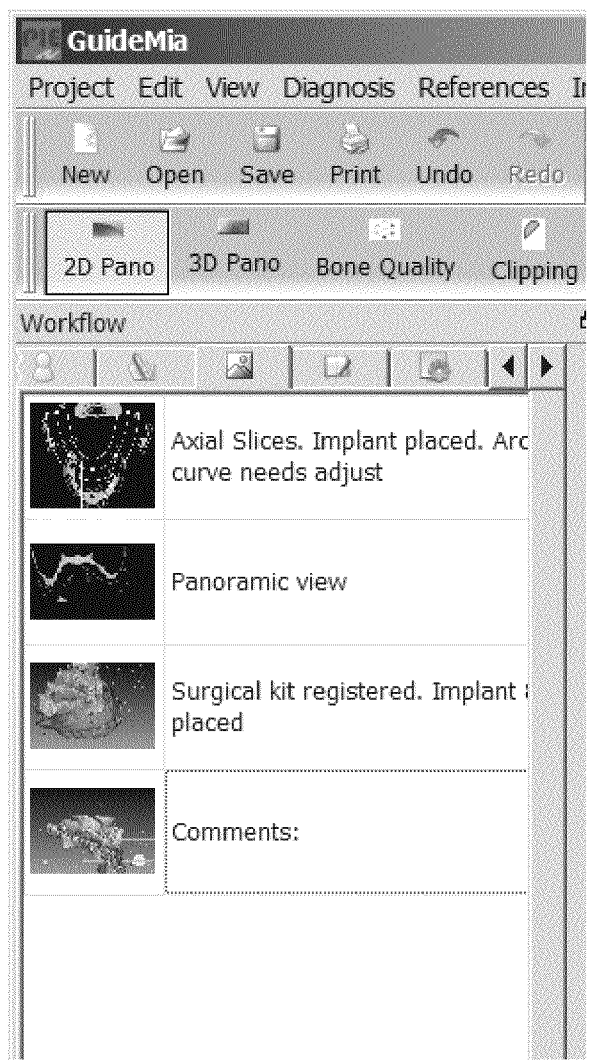

A new mechanism derived from the associative workflow is the snapshot of the workflow, which is defined as the combination of workflow data model, current objects, and visualization settings. In FIG. 7, a class diagram illustrates a specific embodiment, and in FIG. 8 a snapshot navigator shows the implementation.

The abstract class SSnapshot is inherited by SViewSnapshot2D and SViewSnapshot3D, the subclasses for snapshots of 2D and 3D windows.

It also has a reference to the working segment and filter, which defines a state of the workflow. The concept "segment" means any data or object derived from the initial CT scan or additional external data such as a STL surface model. For example, a bone structure is a segment in the treatment planning built upon a series image processing filters. In consequence, a snapshot also has the reference to the active filter, named as workingFilter.

A snapshot has the visualization parameters. Camera settings and a capture of the image window are defined in the abstract class. The subclasses will have additional information accordingly. For example, SViewSnapshot2D has window/level information for the gray level display of CT slices, while SViewSnapshot3D has color map, opacity map, cutting plane, etc.

Additional information such as annotations and comments are also saved with the snapshot object.

A snapshot belongs to the underlying data model, an instance of SStudy, and hence will be also saved in project files together with other objects.

All the snapshots are listed in the snapshot navigator, which provides the management functions.

With this approach, a snapshot essentially captures the workflow status and the way to present the data in the image windows. With all the data model and workflow status available, the software system of this invention provides a function to make a snapshot current. That is, to bring the workflow data to the status when the snapshot is created, to set the visualization parameters to the saved ones, and to render the objects in image windows accordingly. When objects have been created after the segments, the suppressing method mentioned earlier will be invoked, so that the objects for the snapshot can be in the right status. As a result of such a "make current" operation, the system enters a specific status saved in the snapshot. Therefore the snapshot is "re-enterable", which is the fundamental advantage of this approach over the commonly found "snapshot" concepts and implementations.

This re-enterable snapshot has many benefits. First, it provides a mechanism to enter specific point of a workflow. Secondly, it provides a better tool than undo/redo or an alternative when revising or revisiting operation history is required. Thirdly, for software developers, this is a tool to do software regression test. Once the system re-enter the state defined by a snapshot, the image display can be compared with the image saved with the snapshot. Any difference may indicate algorithm changes or regressions.

Design for Manufacturability and Applicability

The Approach

Models resulted from only the voxels of the bone structure tend to have artifacts. It is even more so when the bone is loose, as illustrated in FIG. 9. These artifacts will make it very difficult to manufacture the guides, or not possible to use the fabricated guides without manually cleaning up the model.

Figure 13:
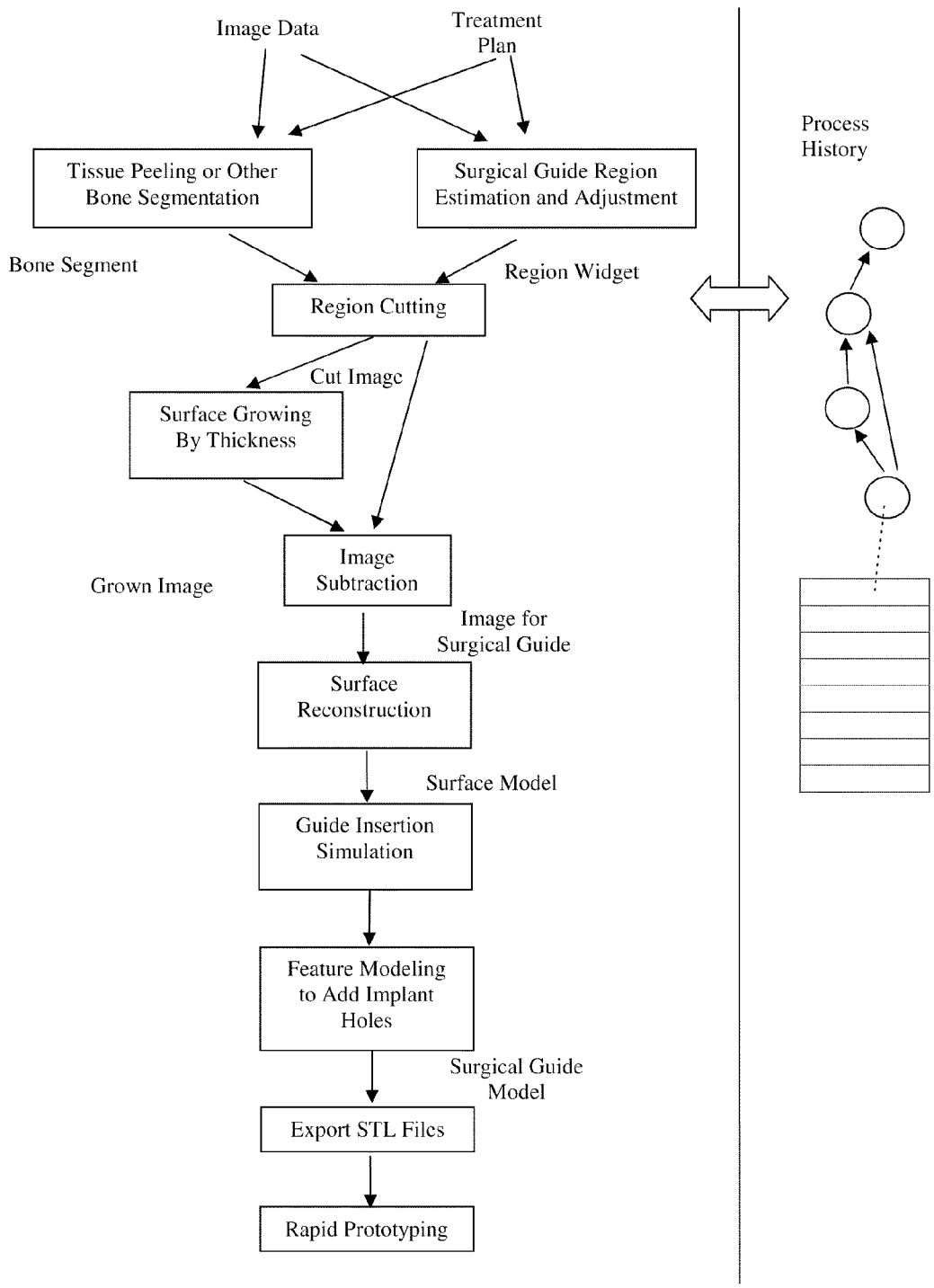

In this invention, surgical guides are designed based on modified models of the bone structures or radiographic guides. The overall workflow of using bone structure is shown in FIG. 13. First, the image data is cut by a given region. The bone segmentation is then performed on the region. Next, the bone model is grown by a given thickness. Then the bone model is subtracted from the grown model. Surface reconstruction applied onto this model will get a closed solid model, which serves the base for further modeling operations.

All this process is backed by the data model and the workflow described in the previous sections.

The bone structure is segmented with a soft tissue peeling simulation. The algorithm is as following, and illustrated in FIG. 11.

1. The bone structure in FIG. 11A is simply segmented with a thresholding filter. A dynamic threshold adjustment tool is used for the users to adjust the window/level to a good setting.
2. A surface-growing algorithm is then employed to grow the image in FIG. 11B so that the small holes or dents can be filled with the soft tissue voxels. Dilating filter, mean filter, etc are used for this surface growing. This produces image in FIG. 11C.
3. Then a surface-peeling procedure is applied to the grown image in order to remove the voxels that don't serve this "filling" purpose. As a result, the image shown in FIG. 11D is better for downstream steps.

What makes this invention different is the fact that the surgical guides are designed based on a mixture of voxels representing both bone and soft tissue, which is congruent with the reality when the soft tissue is peeled the process will just reveal most of the bone structure, but leave soft tissue in some small areas in place. The process actually forms a better base for the guide placement and surgery than a thorough soft tissue peeling does. The algorithm listed above is called "design for manufacturability and applicability".

As second part of this method, also important is a region selection tool for the users to select the area of the bone structure, or radiographic guide, from which the surgical guide will be designed. Normally, it is not necessary for the guide to cover the entire bone structure or radiographic guide. Based on the implant parameters, positions, orientations, as well as the surgical kits being used, a heuristic approach is developed to estimate the spatial range of the surgical guide. This range is displayed to the users so that they can interactively adjust it. This adjustment will help exclude the areas that either are not necessary or tend to cause problems due to the bone deficiency and other similar problems.

As illustrated in FIG. 13 the image data is then cut by the selected region and grown bigger by the thickness of the surgical guide. A subtraction operation is performed between the images before and after the growing operation. The outcome of this step is the image data corresponding to a model of the surgical guide. A surface model is then obtained by reconstruction approaches. After this, all other steps for the surgical guide design are based on this model.

A guide insertion simulation is performed next. Certain range of spatial angles will be defined based on the orientations of the implants. Further model cleanup will be used to eliminate undercuts that will prevent the guide from being inserted in or pulled out. Moreover, areas that still have large curvature will be evaluated and smoothed out if necessary. The algorithms will include using curvature analysis, filtering, Gaussian smoothing, point reduction in a triangulated model, etc.

Together the steps mentioned above create a surface model that has no or minimum manufacturability or applicability problem. The final surgical guide design based on this model will be good for the surgery.

CAD/CAM Solution

In the lower part of FIG. 13 is the integration of CAD/CAM. It has three components, namely, the feature-based modeling, STL file export and Rapid Prototyping (RP). By RP, we mean any additive manufacturing technologies that build a solid model in by adding materials layer by layer or point by point. Stereo lithography (SLA) and 3D printing are examples.

As describe above the base models of surgical guides, without the artifacts resulted from bone segmentation, will better fit the patients' anatomy.

The feature modeling is based on boundary representations, which is much more accurate and practical. As a matter of fact this has become the standard CAD approach, while voxel-based method is rarely found now. In the modeling system, a solid model is represented as closed shells; a shell is represented as faces, a face as edges, and an edge as two vertices. Solid modeling engines have been well established to perform feature operations with the boundary model. With triangulated model generated from the surface reconstruction, the modeling engine has some special techniques to deal with the facts that faces all have three edges, and that there are normally a huge number of faces. A good nature of feature-based modeling is the associativity. As mentioned earlier, the concept of associativity stems from CAD area. Introducing feature-based modeling will keep the entire workflow associative.

In order to make the surgical guides, any CAM technology taking CAD files can be used. In our system we integrate RP technology, which is becoming the standard approach to the manufacturing of any triangulated models.

This integration is very different from the approach of Swaelens (U.S. Pat. No. 5,768,134), which tries to create form features by a voxel based approach and does not have a clear differentiation of CAD and CAM when RP processing is claimed to be used for both CAD and CAM operations.

This integration is different from conventional CAD/CAM approach, where a model is typically created from the scratch.

It is also different from reverse engineering applications. This integration starts the design from a based model generated by image processing with manufacturing considerations, while reverse engineering systems typically start from a point cloud and surface reconstruction.

Surgical Kit Driven Guide Design
Surgical Kit in Guide Design

Only the surgical kits for tissue-borne surgical guides are described in this application. For bone-level guides, the concepts and techniques are essentially the same.

Figures 14, 15:
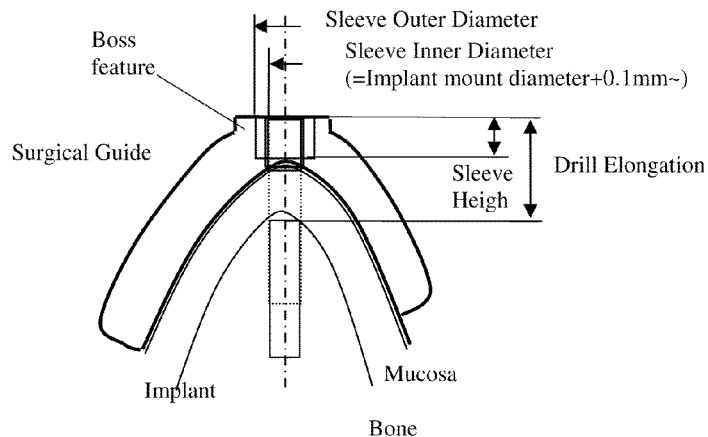

FIG. 14 shows that how a surgical guide is designed with one implant as example. The base is the surface model of the radiographic guide, and can be a model created based on bone structure as well. The area corresponding to an implant location is made of a couple of form features, whose geometries and parameters depend on the implant and surgical kit. The hole on the top of the guide is to hold the drilling sleeve. Sleeves are specifically made according to the implant diameters. The inner diameter of the sleeve is slightly bigger than the diameter of the final drill. In the actual surgery, after a hole is drilled on a patient's jawbone and an implant is placed, a so-called implant mount will be inserted into the place to cover the implant while the surgical guide may be still in place. In this situation the final drill's diameter is actually the outer diameter of the implant mount. It can also be simply the implant diameter when no implant mount is used, or when implant mount is designed to be at same or smaller size.

Second form feature that matters is the boss feature that has a planar top face as the entrance of the hole. The normal direction of the face is determined by the implant orientation, and the location determined by the surgical kit being used. The distance between this face and the apical center of the implant is a delta plus the implant depth. The surgical kit will need to have a drill that can go this far and has a drilling stop at this distance. This delta is referred as the elongation value of the drill, or of the surgical kit. Practically one does not want to have various values for various implant sizes. Vendors might have just one value for all. For example, NobelReplace uses 9 mm for this. However, there could be of course the design that individual drill has its own elongation value.

On the other hand, if the surgical kit to be used does not have such thing as drill stop, it is not very necessary to define this elongation value. Nevertheless for the convenience of the surgeons or the sake of safety, it is important to define some value and notify the doctors in a specially generated drill instruction. This elongation does not matter at all when the surgical guide is only used for pilot drills, wherein the surgeons will do freehand drilling after the pilot drill.

Meanwhile, as a whole, a surgical guide also has some features that are determined or driven by the surgical kit. For example, there could be irrigation windows on a guide so that the surgeons can flush the implant area with special tools designed for this purpose. This irrigation tool is part of the surgical kit in a broader sense.

Therefore the major form features of a surgical guide depend on the surgical kits being used. On one hand, the surgical guide CAD system needs to define the surgical kit configurations based on the actual kits in order to derive the feature dimensions. On the other hand, the configurations can serve as guidelines for the development of surgical kits.

Surgical Kit Configuration

In order for the parameters of a surgical kit to directly drive the surgical guide design, this invention includes a method and software module to configure surgical kits.

Figures 16, 17:
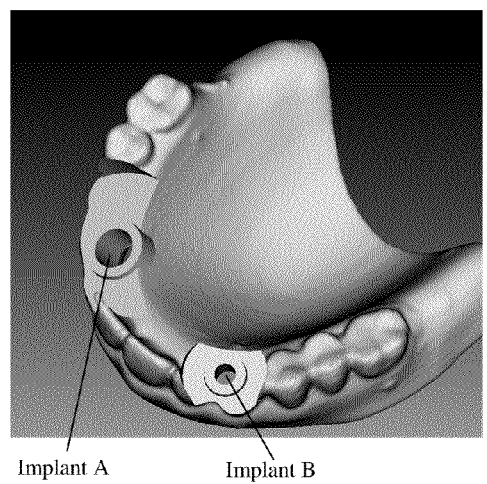

In FIGS. 15 and 16 specific embodiments of surgical kit configuration are illustrated by two screenshots. A kit includes a few platforms according to the implant platforms. For example, the kit definition of NobelReplace includes a narrow platform, regular platform and wide platform corresponding to implant of three sizes. Each kit platform is defined as the implant mount diameter, the outer diameter of the sleeve, the mating gap between the sleeve and the drill, the drill elongation, etc. Strictly speaking, the sleeves are not part of a surgical kit. They are included in this kit configuration tool because they work with the kit options to determine the parameters of the guides.

What differentiates this invention from other software systems is that this surgical kit configuration is open to the users with a unique and clear definition, and the surgical guide modeling operations are derived from and associative with the kit configuration.

In addition, this configuration has not only the key parameters of the surgical kits. It actually includes the design of the sleeve. In the manufacturing of surgical guides, the labs need to make the holes with the outer diameters of the sleeves, and also make sleeves to insert into the holes. Moreover, the sleeves and guides will have features so that the glues can be injected into. Therefore the design of the sleeves is part of the surgical guide CAD/CAM. With this invented configuration tool, users can not only define the kit parameters, but also consider the actual settings for manufacturing the guide. In other words, this offers an open system architecture that makes it possible for any dental lab to put their sleeve settings into the software system so that the surgical guides can be designed following their guidelines.

Hybrid Usage of Surgical Kit in a Single Case

Another differentiator of this approach is the hybrid method using surgical kits in guide design, which helps the cases where using only one surgical kit in one case for all implants may not be feasible. This is mentioned in the background section.

In this invention, the hybrid usage of surgical kit is included to address the above issue, which has not been found in publications or commercial systems. In one embodiment, if the diameter of an implant is not found in any of the platforms of a surgical kit definition, the system will create form features for this implant location just for the drill of a pilot hole, while other implant locations are fully designed with the surgical kit in use. In another embodiment, the users can select different brands or models of implants, and surgical kits for different implants as long as the guide design and clinical condition justify this. FIG. 17 illustrates the situations that one implant is defined for using surgical kit, the other not. Implant A is for the surgical kit so the hole is bigger, while the hole corresponding to implant B is for the 2 mm pilot drill.

Surgical Kit Conceptual Design Tool

Figures 18, 19:
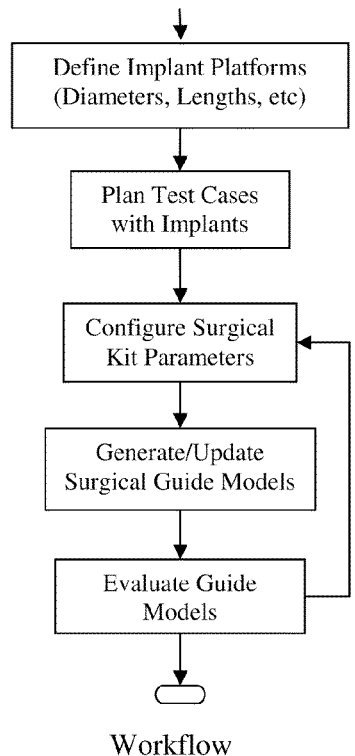

This kit configuration is further implemented as a tool for surgical kit vendors to conceptually design and validate their surgical kits. FIG. 18-20 illustrates how this is accomplished. FIG. 18 is the workflow chart. FIGS. 19 and 20 are the screen capture of related tools. A vendor has a series of implants with different diameters and lengths. They are defined with an implant library management tool. Its design engineers define the basic parameters using this configuration tool corresponding to the implant sizes. Moreover, they use a set of treatment planning cases to place those implants, generate surgical guide models with underlying surgical kits, and then verify and validate the surgical kit parameters by evaluating the generated surgical guide models. With this process they can find the problems with the kit design. For example, if the chosen elongation distance is too big, the generated guide will have boss feature that is too high.

Even better, the surgical kit parameters can be further adjusted to drive the guide design with the support of the associative workflow in this invention. In a specific embodiment, certain parameters of the kit definition can be given a series of values, and the test cases are updated according to these values in a predefined batch mode. This results in a series models for each surgical case. The engineers can evaluate the models and choose the good parameters.

What is claimed is:

1. A computer system for dental implant treatment planning and surgical guide design and manufacturing, comprising
    a) a computer hardware system with an operation system,
    b) an implant planning software system installed on said computer and run in the RAM of the computer,
    c) a data input means to make image data and any geometric models acquired by CT scanners and optical scanners available to the treatment planning software,
    d) a software component to process and transfer said image data and geometric models into graphical display in the computer monitor,
    e) a software component to simulate implant placement by placing and visualizing digital models of implants with said image data and said display,
    f) a software component to combine image data and geometric models, as well as the parameters of said implants, and further to generate a surgical guide model for the said image data,
    g) a rapid prototyping equipment,
    h) a means to send said surgical guide into the manufacturing equipment, where the surgical guide is manufactured,
    wherein improvements include
    a) fully data associativity throughout the data models from planning to design and manufacturing,
    b) a means to update data that will propagate any changes in the image processing and implant placement into surgical guide design and then into the manufacturing equipment,
    c) an integrated means to navigate and manage treatment planning and surgical guide design in a single user interface widget,
    d) a means to design surgical guides according to surgical kit,
    e) a boundary representation based approach to represent geometric models throughout treatment planning, surgical guide design and manufacturing, and integrate the components,
    whereby treatment planning, surgical guide design and manufacturing are integrated into one integral workflow and one computer system, and no external means to process any of the data or models is needed.

2. The computer system according to claim 1, further including
    a) a means to define and save specifications for implant surgical kits, which include drilling sleeves and drills, and specifications of the geometric shapes and dimensions of the drilling sleeves,
    b) a means to select a surgical kit specification from the saved specifications for the implants placed with said image data,
    c) a means to create implant holes on the surgical guide model according to surgical kit specification, and
    d) an update means to update the surgical guide model according to the editing or reselection of the surgical kit,
    whereby the surgical guide is designed driven by the parameters of the surgical kit and to be used with said surgical kit.

3. The computer system according to claim 2, further including
    a) a means to convert selected surgical kit specification into geometric form features, which
        i. comprise drill holes and drill-stop faces, and
        ii. will be added onto the surgical guide models for further manufacturing,
    whereby an open architecture is offered by the software system for dental labs to control or customize surgical guide design according to their own surgical kit configurations.

4. The computer system of claim 3, further including a means to configure a surgical kit, wherein
    a) the surgical kit is defined as a plurality of implant platforms,
    b) a platform corresponds to a particular implant of particular platform from an implant manufacturer,
    c) the platform is defined as a set of parameters including the diameter of said implant and its implant mount, a thickness value of a drilling sleeve that is used for said implant in guided surgery, and an elongation value that a drill should have, and
    d) surgical guide design is driven by the definition of the platforms of the implants in a clinical case.

5. The computer system of claim 4, wherein
    a) each individual implant of a clinical case can have its own surgical kit choice,
    b) one clinical case can use implants from multiple platforms and multiple surgical kits accordingly, and
    c) the surgical guide is designed for multiple platforms of implants,
    whereby the mixing of the implant platforms as well as surgical kit platforms offers a great flexibility for image guided surgery.

6. The computer system according to claim 1, wherein an image processing means is used to segment tooth and bone structures of a patient, comprising
  a) a step to grow bone model to close small holes on the bone structure, and
  b) a step to peel the grown model to the bone surface,
  whereby such a procedure to simulate peeling soft tissues is employed to generate smooth bone and tooth structure, which follows the actual bone/tooth contour well enough for surgical guide purposes.

7. The software system according to claim 6, wherein the surgical guide is designed by
  a) extracting an area from said segmented bone/tooth model after tissue peeling simulation,
  b) offsetting the extracted surface model, and
  c) adding geometric features for drill holes,
  whereby the resulted surgical guide will be smooth and can fit onto the bone/tooth model with tissue peeled instead of from thresholding, and in consequence, the surgical guide has better manufacturability than a model created by wrapping just the bone/tooth structure.

8. The computer system of claim 1, further including:
  a) an internal data model that represents not only images and geometric models, but also an operation history with operations represented as timestamps and dependencies,
  b) a dependency graph among operations of image processing, surface reconstructing from 3D images, geometric modeling with the surface model, as well as configuring and selecting surgical kit, whereby any changes in earlier stage can be automatically propagated to the downstream,
  c) a project file that accordingly stores images, models, as well as the operation history,
  d) a history navigator that renders said images, models and operations as nodes on a treelist as a common user interface means, and performs data management and browsing of them,
  e) a means to edit, suppress, unsuppress, or delete the nodes in the history navigator, and
  f) a means to replay the history tree from scratch to rebuild the entire processing pipeline and regenerate the treatment plan and surgical guide design from the original scan data,
  whereby a full associativity among the operations and models is maintained, and any parameter changes can be propagated to downstream operations and models in the operation history.

9. The computer system of claim 1, which further includes
  a) a workflow snapshot, which is defined as a combination of a system status comprising an object of interest that is a node in said history navigator, as well as display options of said object,
  b) a means to save and retrieve the data of a snapshot, and
  c) a means to set the treatment planning module of the said computer system to the status where the snapshot is defined, and to restore the display of said object of the snapshot by display options when the snapshot is defined.

10. The computer system of claim 1, wherein a user interface means and surgical guide update module are provided so that the surgical guide at an individual implant location is designed
  a) to be congruent with the corresponding surgical kit platform, whereby, its drill hole on the surgical guide is based on the parameter of user selected surgical kit, or
  b) to be congruent with the surgical kit platform that is only for a pilot drill that is smaller than an implant.

11. The computer system of claim 1, which further provides a process to perform the conceptual design of a surgical kit by
  a) providing the means to configure the surgical kit,
  b) providing test cases with predetermined implant locations and orientations,
  c) planning implants from the implant platforms defined in the surgical kit,
  d) designing the surgical guides accordingly,
  e) and providing a means to evaluate the surgical guide and validate the surgical kit definition.

12. The computer system of claim 1, wherein
  a) treatment planning, surgical guide design and its computer-aided manufacturing are integrated,
  b) the surgical guide is designed according to surgical kit,
  c) the base model of the surgical guide is a geometric model represented by boundary representations comprising triangles and their adjacency information,
  d) the surgical guide model is created by adding form features to said base model, other than directly from image data,
  e) the surgical guide is also represented as boundary representation and saved as a file on a storage media or as a data structure in internal memory,
  f) said file or data structure without any form feature parameters is sent to rapid prototype equipment for manufacturing,
  whereby the design and manufacturing of the surgical guide is integrated in one system, and the boundary representation of the surgical guide offers the flexibility to adapt to various input data.

13. The computer system of claim 12, wherein
  a) The base model is constructed by one of, but not limited to, the following means and data sources:
    i. creating a contour surface of the bone/tooth model resulted from simulating the soft tissue peeling,
    ii. creating a closed contour surface of a CT scan of a radiographic guide,
    iii. extracting a surface area of a CT scan of a radiographic guide, or
    iv. acquiring an optical scan of a patient's oral-dental anatomy or a plaster model of the anatomy,
  b) the base model of the surgical guide is a pure geometric data model without having to carry original medical or image information from the input scan data of any kind,
  c) a means of data abstraction is built upon the base model, which is independent of the said data sources of anatomy, impression, stone model, and radiographic guide, or any others,
  d) a data processing pipeline built upon the base model is provided as a means to integrate treatment planning and surgical guide design, and later on the manufacturing, and
  e) the data abstraction based on the base model provides an unique process that is independent of the modality of the data source of a treatment plan case,
  whereby the integration of the treatment planning, surgical guide design and manufacturing can be adaptive to various input data and treatment planning protocol.

* * * * *